United States Patent [19]

Tieke

[11] Patent Number: 5,030,742
[45] Date of Patent: Jul. 9, 1991

[54] ULTRATHIN LAYERS OF PALLADIUM(O) COMPLEXES

[75] Inventor: Bernd Tieke, Obernburg, Fed. Rep. of Germany

[73] Assignee: Ciba-Geigy Corporation, Ardsley, N.Y.

[21] Appl. No.: 444,467

[22] Filed: Dec. 1, 1989

[30] Foreign Application Priority Data

Dec. 16, 1988 [CH] Switzerland ............... 4662/88

[51] Int. Cl.$^5$ .............................. C07F 15/00
[52] U.S. Cl. ........................... 556/136; 556/2
[58] Field of Search ................... 556/136, 2

[56] References Cited

U.S. PATENT DOCUMENTS

| | | | |
|---|---|---|---|
| 3,993,807 | 11/1976 | Stabenow et al. | 427/229 |
| 4,347,232 | 8/1982 | Michaelson | 423/584 |
| 4,622,411 | 11/1986 | Sirinyan et al. | 556/136 |
| 4,632,996 | 12/1986 | Larock et al. | 556/136 X |
| 4,756,848 | 7/1988 | Tieke et al. | 252/511 |

FOREIGN PATENT DOCUMENTS

| | | |
|---|---|---|
| 969163 | 6/1975 | Canada . |
| 0125617 | 11/1984 | European Pat. Off. . |
| 0214097 | 3/1987 | European Pat. Off. . |
| 0233145 | 8/1987 | European Pat. Off. . |

OTHER PUBLICATIONS

Houben-Weyl, "Methoden der Organischen Chemie,", 4th Ed., vol. XIII/9b, p. 714 (1984).

Primary Examiner—Arthur C. Prescott
Attorney, Agent, or Firm—Stephen V. O'Brien

[57] ABSTRACT

Monolayer or multilayer systems containing a 1,5-diarylpenta-1,4-dien-3-one-palladium(O) complex of formula I

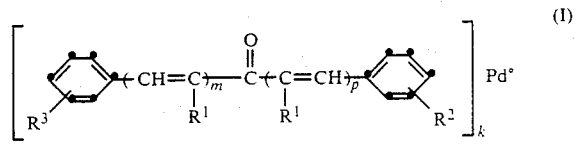

wherein both the groups $R^1$ independently of the other are hydrogen or $C_1$–$C_4$alkyl or both the groups $R^1$ together are a polymethylene chain containing 2–4 C atoms, $R^2$ is hydrogen, $C_1$–$C_{22}$alkyl, $-N(R^4)_2$, $-NO_2$ or $-CN$, $R^3$ is $C_1$–$C_{22}$alkyl, $R^4$ is $C_1$–$C_{22}$alkyl, $k = 1-3.5$, $m = 1-3$ and $p = 1-3$, are excellently suitable for electroless metallization, as sensors for $H_2$ detection or as catalytically active surfaces for hydrogenation processes.

7 Claims, No Drawings

ULTRATHIN LAYERS OF PALLADIUM(O) COMPLEXES

The present invention relates to monolayer or multilayer systems containing palladium(0) complexes, to a process for their preparation, to a process for the activation of substrate surfaces containing such monolayer or multilayer systems, and to the use of these layer systems for electroless metallization, as sensor materials for hydrogen detection or as catalytically active surfaces for hydrogenation reactions.

European patent application 0 125 617 discloses a tetrakis(triphenylphosphine)-palladium(0) complex which can be decomposed by heat and which forms Pd° metal films.

Other palladium(0) complexes are mentioned in Houben-Weyl "Methoden der organischen Chemie (Methods of Organic Chemistry), 4th edition, vol. XIII/9b, Metallorganische Verbindungen (Organometallic Compounds)", p. 714/5, Verlag Georg Thieme, Stuttgart, 1984.

European patent application 0 233 145 discloses thin polymer films containing a dibenzalacetone-palladium complex in dissolved form, which can be activated by heat for electroless metal deposition. However, the smallest possible film thicknesses here are ca. 1 μm.

Furthermore, U.S. Pat. No. 4,347,232 discloses the use of dibenzalacetone-palladium complexes, dissolved in the organic phase of a two-phase system consisting of water and an organic solvent, as catalysts for the preparation of hydrogen peroxide from hydrogen and oxygen.

European patent applications 0 190 998 and 0 214 097 disclose the use of dibenzalacetone-palladium complexes for electroless metal deposition.

An important prerequisite for the preparation of monolayer and multilayer systems by the Langmuir-Blodgett (LB) technique is firstly the ability of the molecules to form stable monomolecular films on the water surface and secondly the ability of the monolayer to attach to solid substrates when they are immersed and/or withdrawn.

Surprisingly, it has now been found that certain palladium (0) complexes, which in terms of their molecular structure do not correspond to the conventional amphiphiles comprising a hydrophobic alkyl chain and a hydrophilic head group, both on their own and in mixtures with other amphiphilic compounds form stable monolayers which can be attached to substrates.

The present invention relates to monolayer or multilayer systems containing a palladium(0) complex.

Complexes which are especially suitable for such monolayer or multilayer systems are 1,5-diarylpenta-1,4-dien-3-one-palladium complexes, in particular those of formula I

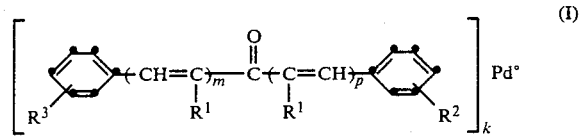

wherein both the groups $R^1$ independently of the other are hydrogen or $C_1-C_4$alkyl or both the groups $R^1$ together are a polymethylene chain containing 2-4 C atoms, $R^2$ is hydrogen, $C_1-C_{22}$alkyl, $-N(R^4)_2$, $-NO_2$ or $-CN$, $R^3$ is $C_1-C_{22}$alkyl, $R^4$ is $C_1-C_{22}$alkyl, $k=1-3.5$, $m=1-3$ and $p=1-3$.

$R^1$ as $C_1-C_4$alkyl is e.g. methyl, ethyl, n-propyl, isopropyl, n-butyl, isobutyl, sec-butyl or tert-butyl.

$R^2$, $R^3$ and $R^4$ as $C_1-C_{20}$alkyl are either linear or branched alkyl substituents. Linear radicals are preferred. Specific examples of such alkyl radicals are methyl, ethyl, n-propyl, isopropyl, n-butyl, isobutyl, n-pentyl, n-hexyl, n-heptyl, n-octyl, 2-ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Preferred monolayer or multilayer systems are those containing complexes of formula I wherein $R^1$ is hydrogen, $R^2$ is $C_1-C_{12}$alkyl and $R^3$ is $C_1-C_{12}$-alkyl.

Especially preferred monolayer or multilayer systems are those containing a complex of formula I wherein $R^1$ is hydrogen, $R^2$ and $R^3$ are each isopropyl in the p-position and k has the value 2.5.

The term "monolayer or multilayer system" will be understood quite generally as meaning any arrangement containing the complexes of formula I in the form of a thin layer or a sequence of thin layers. The term "thin layer" will be understood in the context of this description as meaning a layer having the thickness of one or more molecular layers.

Such monolayer or multilayer systems are preferably a monomolecular layer or a sequence of monomolecular layers containing complexes of formula I which can be obtained by transfer on to solid substrates by the Langmuir-Blodgett process (LB process).

Some of the complexes of formula I are known and can be prepared by processes known per se (q.v., for example, J. Chem. Soc. D, 1970, 1065 and U.S. Pat. No. 4,347,232) by reacting k mol of a compound of formula II

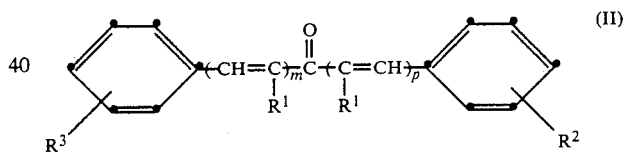

with a soluble palladium salt in the presence of a base and, if necessary, an H donor, $R^1$, $R^2$, $R^3$, k, m and p being as defined for formula I.

Examples of bases which can be used are alkali metal salts of aliphatic monocarboxylic acids, in particular potassium and sodium acetate. $PdBr_2$, $PdCl_2$ and $Na_2PdCl_4$ are examples of suitable palladium salts. It is especially preferred to use $Na_2PdCl_4$ and, in particular, $PdCl_2$. The reaction is conveniently carried out in an organic solvent which also acts at the same time as an H donor. Examples of solvents which are suitable for this purpose are alkanols containing up to 6 C atoms, in particular ethanol and most preferably methanol.

The compounds of formula II can be prepared in a manner known per se, for example by a process analogous to that described in U.S. Pat. No. 4,347,232.

The asymmetrically substituted dibenzalacetone derivatives are synthesized by known methods, e.g. Ber. dt. Chem. Ges., 14, 2471, (1881) and 46, 3813, (1913), in two steps:

Surprisingly, stable monomolecular layers can be prepared at the water/gas interface from the complexes of formula I. To do this, a small amount of a solution of a complex of formula I in a preferably low-boiling and water-immiscible solvent is applied to the free surface of a water subphase in a manner known per se, the solvent is allowed to evaporate and the resulting film is compressed to form a stable monomolecular layer on the surface of the water subphase.

The subphase, on which the monomolecular layer is formed, normally consists of multidistilled or deionized and filtered water to which small amounts of salts, for example $CdCl_2$ or $BaCl_2$, may be added to stabilize the films. The subphase can also contain buffer substances, for example $NaHCO_3$. These modifications are known to those skilled in the art and are chosen in accordance which the nature of the film-forming substances.

It is common knowledge that the stability of the films can be influenced by the choice of experimental parameters. Thus, for example, relatively labile films of complexes of formula I can be stabilized by cooling the subphase, or complexes of formula I are used in conjunction with other suitable amphiphilic compounds which are able to stabilize monomolecular films.

Examples of preferred amphiphilic compounds are long-chain fatty acids such as palmitic acid, stearic acid, arachidic acid, behenic acid or melissic acid, or esters of these fatty acids, in particular the methyl esters; long-chain sulfonic acids and phosphonic acids, esters thereof and long-chain sulfates and phosphates; long-chain alcohols such as n-pentadecanol, n-octadecanol, n-eicosanol or n-triacontanol; long-chain primary amines such as n-hexadecylamine, n-eicosylamine, n-docosylamine or n-triacontylamine; or long-chain amides such as stearamide. The term "long-chain" will be understood as meaning a carbon chain containing at least 12 C atoms, in particular containing 15-30 C atoms.

The acids are preferably used in the form of salts, in particular Cd salts.

Other compounds which are also suitable for stabilizing monomolecular layers are long-chain aliphatic hydrocarbons such as hexadecane, octadecane or eicosane, and polymers such as polyoctadecyl acrylate or polymeric phthalocyaninatosiloxanes.

Preferred amphiphilic stabilizing compounds are saturated or unsaturated fatty acids or salts or esters thereof.

Accordingly, the present invention further relates to monolayer or multilayer systems which contain an amphiphilic stabilizing component in addition to the complexes of formula I.

The complexes of formula I are normally present in such mixtures in a proportion of at least 1% by weight, based on the total mixture.

Surprisingly, monomolecular films containing complexes of formula I and, if appropriate, other suitable amphiphilic compounds can be readily transferred from the surface of the water subphase to solid substrates by the LB technique. This is done by immersing a solid substrate, in a manner known per se, through a water subphase having on the surface thereof a compressed monomolecular film, whereby said film is transferred to the substrate.

Such films preferably contain 5-100 mol %, in particular 20-100 mol %, of complexes of formula I in conjunction with other components, e.g. amphiphilic compounds, which are able to stabilize monomolecular films.

Multilayer systems can be prepared in this way by repeated immersion and withdrawal of the substrate.

The monofilm present on the surface of the water subphase can be replaced after each immersion and withdrawal, so that different orders of layers can be deposited on the substrate.

The methods of preparing multilayers are known per se to those skilled in the art of LB systems and are described, for example, in "Techniques of Chemistry, Physical Methods of Chemistry, vol. I, part 3B, p. 666-671, edited by: A. Weissberger & P. Rossiter".

Suitable solid substrates for the LB technique are a very wide variety of hydrophilic or hydrophobic substrates with a microscopically planar surface. Examples of such substrates are metals such as aluminium or platinum, semiconductors such as germanium or silicon, inorganic materials such as glass, quartz, ZnS or $CaF_2$, or plastics such as Teflon ®, polymethyl methacrylate or epoxy resins. It is also possible to use substrates which have been made hydrophobic, for example glass or quartz which has been pretreated with silanes such as trichloromethylsilane, dichlorodimethylsilane or trichlorooctadecylsilane, or precoated with several layers of cadmium arachidate.

A material advantage of such LB films compared with e.g. films applied from solutions is that the layer thickness is accurately controlled and defined even for dimensions $\leq 1$ $\mu$m.

The invention further relates to a process for the preparation of monolayer or multilayer systems which essentially comprises the steps of:

(i) preparing a monomolecular layer of a complex of formula I or a mixture of a complex of formula I with other amphiphilic compounds which are capable of stabilizing such layers, and (ii) transferring said layer to a solid substrate by the Langmuir-Blodgett technique by single or repeated immersion and/or withdrawal of said substrate through the layer.

It is preferred to transfer mixed layers of complexes of formula I and carboxylic acids or salts or esters thereof.

By treating the complexes of formula I in the layers on the substrates with heat, in particular at temperatures $\geq 100°$ C., ultrathin homogeneous layers of catalytically active Pd° can be produced from these complexes.

The Pd° clusters formed are catalytically active and catalyze the electroless metallization (e.g. nickel plating, copper plating) of the substrate surface, for example according to the following sheme:

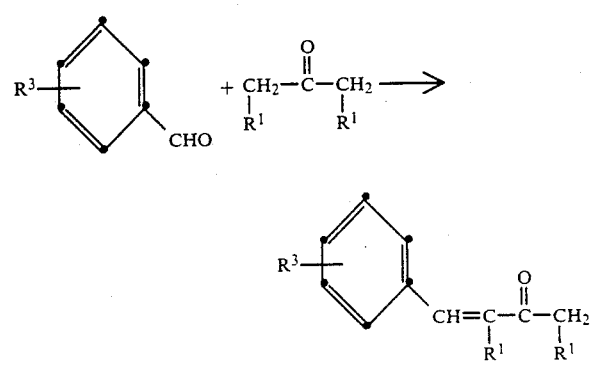

-continued

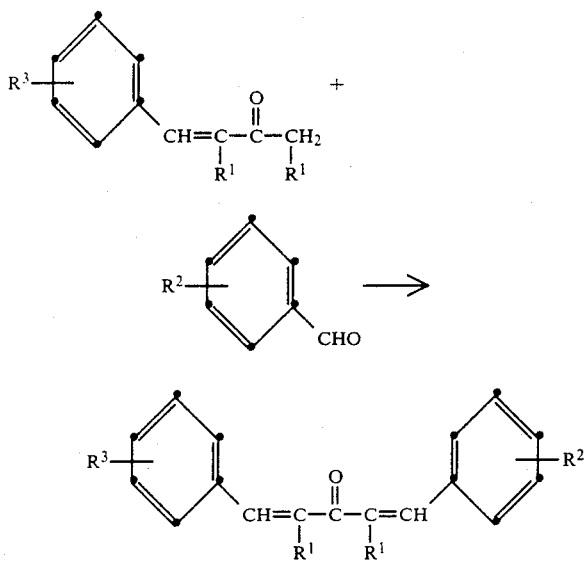

The adhesion of the metal film is excellent. The electroless metal deposition can be carried out using metallization baths known per se and by conventional methods. Examples of suitable metals are copper, nickel, cobalt, silver, gold or tin.

Accordingly, the present invention further relates to a process for the activation of substrate surfaces for electroless metal deposition which comprises the steps of producing a monomolecular layer of a complex of formula I and transferring said layer to a substrate by the Langmuir-Blodgett technique, as defined above [steps (i) and (ii)], and subsequently iii) heating the layer system to a temperature $\geq 100°$ C., whereupon the complex of formula I decomposes and an ultrathin homogeneous layer of catalytically active Pd° is produced.

In addition to their utility as active substrate surfaces for electroless metallization, the activated ultrathin homogeneous Pd° layers can also be used (a) as sensor materials for $H_2$ detection or (b) as catalytically active surfaces for hydrogenation processes, in which case the saving of material in the preparation is an important factor.

EXAMPLE 1

Preparation of the tris(p,p'-diisopropyldibenzalacetone)palladium complex (complex 1) according to U.S. Pat. No. 4,347,232, column 5, lines 37 et seq., affording black-violet crystals of the composition 76.53% C; 7.41% H; 10.9% Pd. Composition calculated for (p,p'-diisopropyldibenzalacetone)$_{2.5}$ Pd: 76.55% C; 7.21% H; 11.8% Pd.

Complex 1 is used without recrystallization for the other Examples.

EXAMPLE 2

Production of monomolecular layers of complex 1 at the gas/water interface

Monolayers are produced at the gas/water interface using a preparative Lauda film balance. The high-purity water needed is freshly prepared with a Milli-Q system available from Millipore and used as the subphase without further treatment. The monomolecular film is prepared by dropping a fresh spreading solution [concentration of complex 1 in CHCl$_3$ (Merck-Uvasol) = 1.0 mg/ml] on to the water surface by standard techniques.

After the solvent has evaporated, the surface-pressure-area diagram is recorded, the film surface being reduced by 12.3 cm$^2$/min. The characteristics of the monolayers are listed in Table 1.

EXAMPLE 3

Preparation of mixed monolayers of complex 1 and cadmium arachidate at the gas/water interface The monolayers are prepared by following the procedure of Example 2. The spreading solution used is a joint solution of complex 1 and arachidic acid in the molar ratio 1:9 [total concentration of the amphiphiles in CHCl$_3$ (Merck-Uvasol) = 1.0 mg/ml]. The subphase is a $3 \times 10^{-4}$ molar aqueous CdCl$_2$ solution which has been adjusted to pH 6.4 with NaHCO$_3$. The characteristics of these monolayers are listed in Table 1.

EXAMPLE 4

Preparation of mixed monolayers of complex 1 and octadecyl sorbate at the gas/water interface The monolayers are prepared by following the procedure of Example 2. The spreading solution used is a joint solution of complex 1 and octadecyl sorbate[1] in the molar ratio 1:6 (total concentration of the amphiphiles in CHCl$_3$ = 1.0 mg/ml). The characteristics of these monolayers are listed in Table 1.

[1] The octadecyl sorbate is prepared as described by B. Tieke, Colloid and Polymer Sci., 263 (1985) 965.

TABLE 1

| | Characteristics of the monomolecular layers at the gas/water interface | | |
|---|---|---|---|
| Example No. | T [°C.] | $\pi^*$ [mN$^c$/m] | $A_c$** [nm$^2$/molecule] |
| 2 | 5,0 | 9 | 0,50 |
| 3 | 15.3 | 53 | 0,20 |
| 4 | 5,0 | 35 | 0,18 |

*$\pi_c$ = film pressure at the collapse point;
**$A_c$ = film area at the collapse point

EXAMPLE 5

Preparation of Langmuir-Blodgett multilayers of complex 1

A monomolecular layer is spread on a subphase of pure water at 5° C. in accordance with Example 2, and compressed to a film pressure $\pi$ of 7.5 mN/m. The temperature and film pressure are optimized so that the monolayer exists in a stable condensed phase. A quartz substrate (30×12×1 mm) precoated with 3 layers of cadmium arachidate is then immersed vertically through the monolayer into the subphase and withdrawn (immersion and withdrawal speeds $S_1$ and $S_2$ respectively). This procedure is repeated several more times, one monolayer being transferred in each immersion/withdrawal to build up the multilayer. The characteristics are listed in Table 2.

EXAMPLE 6

Preparation of mixed multilayers of complex 1 and cadmium arachidate

A monomolecular layer is spread on a $3 \times 10^{-4}$ molar aqueous cadmium chloride solution (pH 6.4, T = 15.4° C.) in accordance with Example 3, and compressed to a film pressure $\pi$ of 20 mN/m. The temperature and film pressure are optimized so that the monolayer exists in a stable condensed phase. A glass substrate (76×26×1 mm) which has been made hydrophobic with octadecyltrichlorosilane (Merck, 98%) is then immersed vertically through the monolayer to a depth of 10 mm into the subphase and withdrawn. This procedure is repeated several more times, as described in Example 5. The characteristics of the multilayer obtained are listed in Table 2.

EXAMPLE 7

Preparation of mixed multilayers of complex 1 and octadecyl sorbate

A monomolecular layer is spread on pure water at 8° C. in accordance with Example 4, and compressed to a film pressure $\pi$ of 10 mN/m. The temperature and film pressure are optimized so that the monolayer exists in a stable condensed phase. A quartz plate (30×12×1 mm) which has been precoated with 3 layers of cadmium arachidate is then immersed vertically through the monolayer into the subphase and withdrawn. This procedure is repeated several more times, as described in Example 5. The characteristics of the multilayer obtained are listed in Table 2.

TABLE 2

Characteristics of the LB films

| Example No | Immersion/ withdrawal speed [cm/min] $S_1(\downarrow)$ | $S_2(\uparrow)$ | number of layers transferred | $\lambda_{max}$ [nm] | $OD_{\lambda max}$ per layer | $d_{001}$* [nm] |
| --- | --- | --- | --- | --- | --- | --- |
| 5 | 2,4 | 1,9 | 6 | 540 | $5,8 \times 10^{-3}$ | |
| | | | | 335 | $3,1 \times 10^{-2}$ | |
| 5 | 2,4 | 1,9 | 14 | 540 | $6,1 \times 10^{-3}$ | |
| | | | | 335 | $3,0 \times 10^{-2}$ | |
| 5 | 2,4 | 1,9 | 80 | 540 | $3,6 \times 10^{-3}$ | 5,45 |
| | | | | 335 | $1,6 \times 10^{-2}$ | |
| 6 | 4,8 | 1,9 | 24 | 540 | $1,4 \times 10^{-3}$ | |
| | | | | 320 | $7,6 \times 10^{-3}$ | |
| 7 | 4,8 | 1,9 | 60 | 540 | $2,3 \times 10^{-3}$ | |
| | | | | 320 | $9,6 \times 10^{-3}$ | |

*determined by X-rays (Philips powder diffractometer)

EXAMPLE 8

Use of the substrates coated with LB films of complex 1 for electroless metallization (a) A quartz substrate coated according to Example 5 (30 layers of complex 1) is heated for 5 min at 180° C. and then immersed in a bath for electroless nickel deposition[2]. An opaque nickel coating has formed on the substrate after ca. 30 minutes.

[2] A commercially available deposition bath for electroless nickel plating, having the following composition according to J. Appl. Electrochem., 1 (1971), 167: 30 g/l $NiCl_2.6H_2O$; 10 g/l $NaH_2PO_2.H_2O$; 50 g/l $NH_4Cl$; 82.4 g/l sodium citrate dihydrate. The pH of the bath is adjusted to 9 with conc. $NH_4OH$. The operating temperature is 90° C.

(b) A quartz substrate coated with 14 layers of complex 1 is used and is heated for 10 min at 160° C. In this case too, an opaque nickel coating has formed after immersion for ca. 30 minutes in the deposition bath.

What is claimed is:

1. A monolayer or multilayer system comprising a 1,5-diarylpenta-1,4-dien-3-one-palladium(O) complex.

2. A monolayer or multilayer system according to claim 1, wherein the palladium complex is a complex of formula I

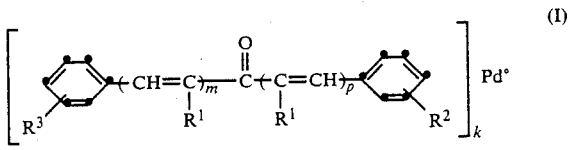

wherein both the groups $R^1$ independently of the other are hydrogen or $C_1$-$C_4$alkyl or both the groups $R^1$ together are a polymethylene chain containing 2-4 C atoms, $R^2$ is hydrogen, $C_1$-$C_{22}$alkyl, $-N(R^4)_2$, $-NO_2$ or $-CN$, $R^3$ is $C_1$-$C_{22}$alkyl, $R^4$ is $C_1$-$C_{22}$alkyl, k=1-3.5, m=1-3 and p=1-3.

3. A monolayer or multilayer system according to claim 2, which comprises a palladium complex of formula I, wherein $R^1$ is hydrogen, $R^2$ is $C_1$-$C_{12}$alkyl and $R^3$ is $C_1$-$C_{12}$alkyl.

4. A monolayer or multilayer system according to claim 2, wherein $R^1$ is hydrogen, $R^2$ and $R^3$ are each isopropyl in the p-position and k has the value 2.5.

5. A monolayer or multilayer system according to claim 2, which comprises an amphiphilic stabilizing component in addition to the complex of formula I.

6. A monolayer or multilayer system according to claim 5, wherein the amphiphilic stabilizing component is a saturated or unsaturated fatty acid, a fatty acid salt or a fatty acid ester.

7. A monolayer or multilayer system according to claim 5, wherein the proportion of the complex of formula I in conjunction with a stabilizing component is 5-100 mol %.

* * * * *